United States Patent [19]
Bonnal et al.

[11] Patent Number: 5,718,712
[45] Date of Patent: Feb. 17, 1998

[54] DILATATION BALLOON CATHETER FOR ENDOSCOPY

[75] Inventors: Olivier Bonnal, Cagnes sur Mer; Christian Sainte-Rose, Vanves, both of France

[73] Assignee: Elekta AB, Stockholm, Sweden

[21] Appl. No.: 513,274

[22] Filed: Aug. 10, 1995

[51] Int. Cl.$^6$ ................................................. A61M 29/00
[52] U.S. Cl. ................................................. 606/194; 606/192
[58] Field of Search ........................ 606/191, 192, 606/198, 194, 195; 604/96, 97

[56] References Cited

U.S. PATENT DOCUMENTS

| | | |
|---|---|---|
| 1,690,995 | 11/1928 | Pratt . |
| 1,786,373 | 12/1930 | Walker ........................ 604/96 |
| 2,849,001 | 8/1958 | Oddo . |
| 2,849,002 | 8/1958 | Oddo . |
| 3,154,077 | 10/1964 | Cannon ........................ 606/192 |
| 3,962,519 | 6/1976 | Rusch et al. . |
| 4,137,906 | 2/1979 | Akiyama et al. ........................ 606/192 |
| 4,213,461 | 7/1980 | Pevsner ........................ 604/96 |
| 4,327,736 | 5/1982 | Inoue . |
| 4,338,943 | 7/1982 | Okamoto et al. ........................ 606/192 |
| 4,351,342 | 9/1982 | Wiita et al. . |
| 4,986,830 | 1/1991 | Owens et al. . |
| 5,355,087 | 10/1994 | Clairborne . |
| 5,360,402 | 11/1994 | Coninay et al. ........................ 604/97 |

FOREIGN PATENT DOCUMENTS

| | | | |
|---|---|---|---|
| 439636 | 7/1912 | France . | |
| 1060-190-A | 12/1983 | U.S.S.R. ........................ | 606/191 |

*Primary Examiner*—Guy V. Tucker
*Assistant Examiner*—Patrick W. Rasche
*Attorney, Agent, or Firm*—Lockwood, Alex, Fitzgibbon & Cummings

[57] ABSTRACT

A balloon catheter is provided which includes a flexible tube on one end of which a balloon is mounted to be inflated by means of the tube, which balloon has an annular restriction in its middle region in a plane approximately perpendicular to the tube axis. The balloon is produced in the form of a bag inside which the end of the tube is engaged, the opening of the bag being fixed to the outer wall of the tube, and the distal end of the balloon projects beyond the distal tip of the catheter tube to provide a cushioning region at the tip of the catheter assembly. A procedure for making the balloon is also described.

16 Claims, 2 Drawing Sheets

DILATATION BALLOON CATHETER FOR ENDOSCOPY

BACKGROUND AND SUMMARY OF THE INVENTION

The present invention relates to a balloon catheter, and more particularly to such a catheter comprising a flexible tube at one end of which a balloon is mounted to be inflated by means of the tube, the balloon additionally having an annular restriction in its middle region and in a plane approximately perpendicular to the tube axis.

The balloon catheter is of the endoscopy type and is sized, shaped and designed to be especially suitable for dilating a hole perforated by laser or electrical bistoury, for example, in the floor of the third ventricle of the brain during a third ventriculostomy procedure. It is designed to be used under endoscopic guidance.

Catheters having an annular restriction are already known, used for example for the enlargement of a stenosis or an orifice artificially created in a membrane. The annular restriction permits the stabilization of the balloon while being inflated, preventing it from sliding to one side or the other of the tissue to be enlarged.

In the known types of catheters, the balloon is produced in the form of a sleeve engaged upon the tube end and bound onto the tube at its two ends, including at its distal end. Such an arrangement generally can be suitable, but on the other hand it is unsuitable in the case where an orifice to be enlarged is located next to a delicate organ. This is for example the case for the treatment of stenosis of the Aqueduct of Sylvius or the supra-sellar arachnoid cyst in cases of hydrocephalus.

Indeed, with these types of prior catheters, the end of the tube, which in these prior configurations protrudes out of the distal end of the balloon, constitutes a danger of perforating such a delicate organ. In other words, the distal end of the catheter body or tube projects distally beyond the distal end of the balloon and often can contact the delicate organ, possibly leading to trauma or damage to the organ.

An important object of the present invention is to overcome these disadvantages so as to minimize or eliminate risk of such organ trauma.

To this end, another object of the invention is a balloon catheter, comprising a flexible tube at one end of which a balloon is mounted to be inflated by means of the tube, the balloon additionally comprising an annular restriction in its middle region in a plane approximately perpendicular to the tube axis, characterized in that the balloon is produced in what might be described as the form of a bag which encloses the distal end of the catheter tube while the annular opening at the proximal end of the bag-like balloon is sealingly affixed to the tube outer wall.

Thus, the tube distal end no longer constitutes a danger as is characteristic of prior devices, inasmuch as the tube does not project beyond the balloon. In a preferred arrangement, when the balloon is inflated, the tube distal end is out of contact with the balloon wall and consequently is totally isolated from the surrounding tissues by the fluid which had been used to inflate the balloon, which fluid provides a cushioning buffer between the distal tip of the catheter tube and the body organ which might engage the inflated distal end of the balloon.

In a particular embodiment of the invention, the distal end of the tube is blocked, and the inflation of the balloon is carried out by means of one or more holes pierced in the tube wall, distal or downstream of the zone at which the balloon is affixed to the catheter body or tube, but proximal of the distal tip of the catheter body or tube. Such affixing of the balloon to the catheter can be by means of heat welding, laser bonding, intermediate polymeric layer, and the like; however, the balloon is preferably secured or affixed by an adhesive approved for in vivo use in humans.

It is especially advantageous to have the balloon stretched onto the tube end prior to inflation. This may facilitate its insertion into place for dilatation in connection with endoscopy and similar types of procedures.

BRIEF DESCRIPTION OF THE DRAWINGS

A particular embodiment of the invention will now be described through non-limiting examples, referring to the accompanying drawings in which.

DESCRIPTION OF THE PREFERRED EMBODIMENTS

Figure 1:
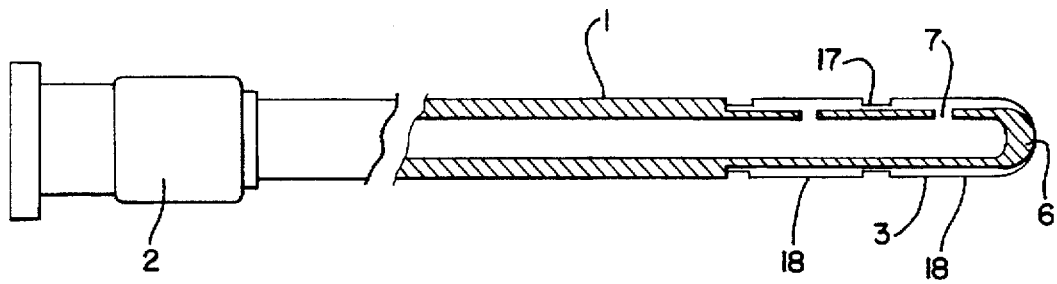
FIG. 1 is a partial axial sectional view of a catheter in accordance with the invention, the balloon not being inflated.
Figure 2:
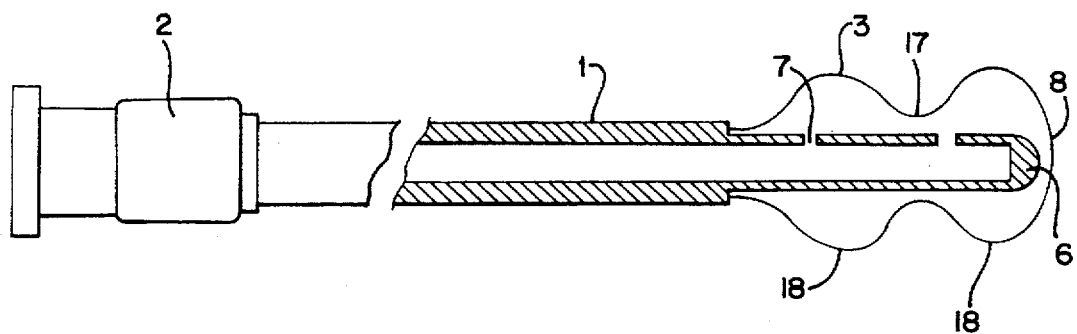
FIG. 2 is a view corresponding to FIG. 1, but with the balloon in an inflated condition.
Figure 3:
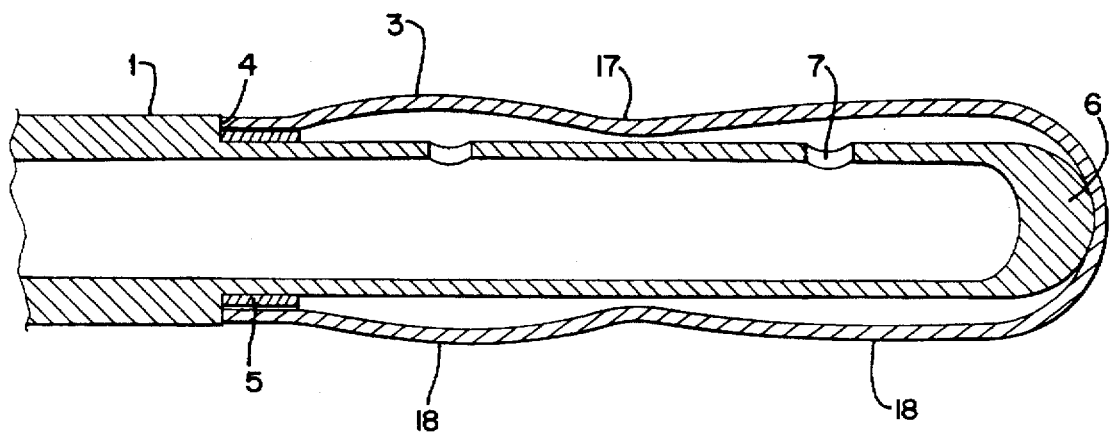
FIG. 3 is a sectional view on an enlarged scale of the distal end of the catheter illustrated in FIG. 1.

The catheter illustrated in FIG. 1 to FIG. 3 comprises a catheter body or tube 1 of any known type, suitable for catheters as described herein. A preferred material in this regard is an extrudable polymer such as a polyurethane. The illustrated catheter includes a Luer adaptor 2 at one of the tube, which is its proximal end. A balloon member 3 is positioned at its other end, which is its distal end.

In accordance with the invention, the balloon member 3 is provided in the form of a "bag" presenting an annular opening 4 (FIG. 6) within which the distal end of the catheter body or tube 1 is engaged. The sides of the opening 4 are mounted on the tube 1. In this illustrated embodiment, the mounting engagement is by interposition of an adhesive ring 5 (FIG. 3) between the inner surface of the balloon member 3 and the outer surface of the catheter tube 1.

As indicated in the drawings, especially FIG. 3, the distal end or tip 6 of the catheter body or tube 1 is closed and preferably curved or semi-spherical as illustrated. Inflation of the balloon 3 is effected by generally known means of the duct or lumen (not shown) of tube 1 and of holes 7 formed in the wall of the tube 1 between the adhesive ring 5 and the blocked or closed distal end or tip 6 of the catheter tube which preferably is in engagement with the balloon, at least prior to inflation.

The balloon member 3 has an annular region 17 of a reduced diameter in a plane approximately perpendicular to the axis of the catheter tube 1 and of the balloon member 3. This annular region 17 is shown in its inflated state in FIG. 2. It is fixed to the tube 1 only by the adhesive ring 5, so that in its inflated state, its distal end section 8 opposite to its annular opening 4 is detached from the distal end or tip 6 of the tube 1. More specifically, this detached or spaced condition is achieved by having the inflation fluid, such as saline solution or the like, between the respective distal tips of the catheter tube and of the balloon member. The result is the important feature of cushioning and/or protection of the body tissues with respect to the distal end or tip of the catheter.

Figure 4:
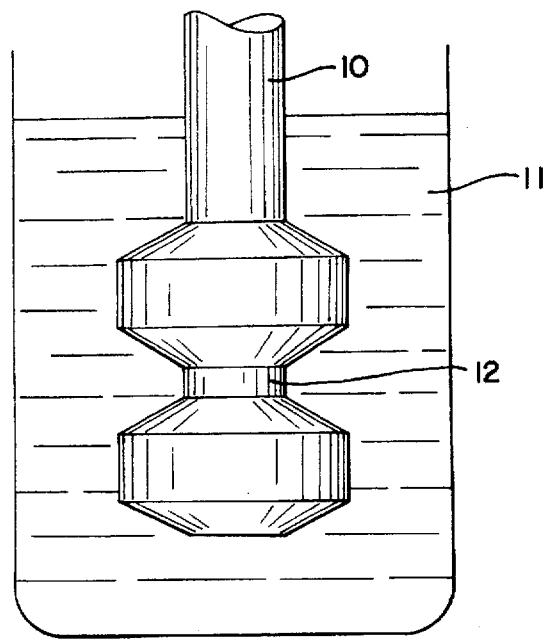
FIG. 4, FIG. 5 and FIG. 6 illustrate three steps of a preferred process and system for manufacturing a catheter according to the present invention.
Figure 5:
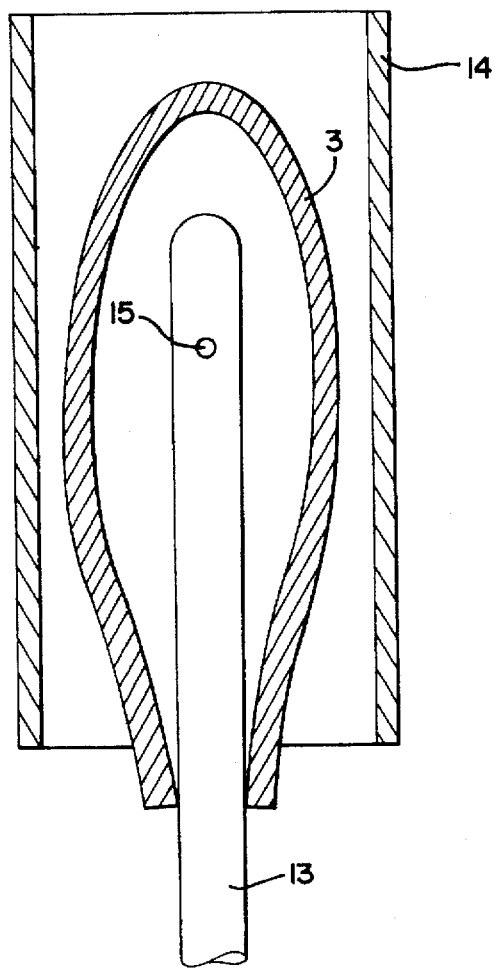
Figure 6:
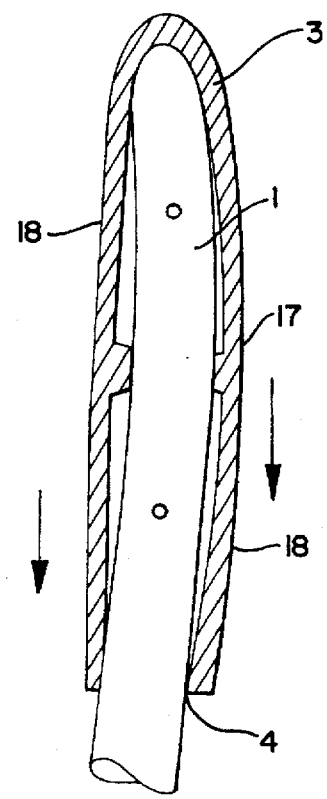

It is preferred that the balloon member 3 is produced by a process and system as generally shown in FIGS. 4, 5 and 6. In this regard, FIG. 4 shows a spindle 10 which is plunged into a bath 11, preferably repeatedly, which procedure forms a film onto the spindle 10 as the material of the bath adheres to and forms on the spindle. The result is a balloon 3 having a shape which substantially conforms to the shape of the spindle 10.

Bath 11 is of a material which will form films on surfaces when exposed to air or the like. Typically, the bath will be a polymer or polymer forming material within a solvent or carrier that dissipates when the solution of the bath is spread in a thin layer. Preferred bath 11 is a solution of silicone compound in heptane, which forms a silicone polymer film or layer upon evaporation or dissipation of the heptane.

The spindle has an end in the form of a dumbbell or a dogbone, having a reduced diameter annular portion 12. When the film or layer deposited by the bath 11 is removed from the spindle 10, the resulting balloon has the general configuration of the outer surface of the spindle 10, which is the desired shape of the balloon member 3 with its annular restriction or region 17 spaced between and partially defining the two illustrated protuberances or balloon regions 18, each of which have a diameter larger than that of the annular restriction 17, especially when the balloon is inflated, as best seen in FIG. 2.

Balloon member 3 thus obtained is introduced onto a rigid tube 13, as illustrated in FIG. 5. Next, this assembly is placed in a tube 14 where the balloon is inflated by means of a hole 15 in the tube 13. During this phase of the process, this tube 14 avoids or prevents bursting during inflation of the balloon member 3.

FIG. 6 illustrates placement of the thus prepared balloon member 3 on the flexible tube 1 (preferably polyurethane). At this time, in accordance with the preferred arrangement, the balloon member 3 is longitudinally stretched along the flexible tube 1 and then adhesively attached in an annular manner around its opening 4 in accordance with the preferred embodiment described herein.

In use, the thus produced catheter typically is introduced through an endoscope working channel using a guidewire. Its balloon is passed through the hole of the third ventricle floor and inflated to render the opening patent. Advantageous cushioning with respect to delicate organs at this location is provided by the inflated distal end of the balloon and its spacing away from the distal tip of the catheter tube. When thus inflated, the balloon presents a "waist" at approximately midway along its length to facilitate placing and retaining of the third ventricle membrane between the two balloon protuberances at inflation, thus preventing the balloon from shifting out of the hole. A typical balloon for this use has a length of about 15 mm, a diameter of about 10 mm at the two protuberances, and a diameter of 5 mm at the "waist" or reduced-diameter annular region 17, the diameters being nominal inflation diameters.

This represents an improvement over prior approaches, including those used to cut a "large" hole in the third ventricle floor by means of laser or electrical bistoury, which might damage the closely positioned basilar artery. Using a Fogarty-type of catheter having a spherical balloon as has been also practiced heretofore presents the difficulties of balloon shifting at inflation. Such an approach requires repeated trial inflations before the dilatation procedure can be successfully completed.

It will thus be seen that the present invention provides a new, useful and important dilatation catheter for endoscopy and the like and procedure for its manufacture which have a number of advantages and characteristics including those pointed out herein and others which are apparent. Preferred embodiments have been described by way of example, and it is anticipated that modifications may be made without departing from the spirit of the invention or the scope of the appended claims.

We claim:

1. An endoscopically guided dilation balloon catheter adapted to dilate a hole in a ventricle of the brain, comprising:

an elongated flexible tubular catheter body having a longitudinal axis, a proximal end portion, a distal end portion and a tip of said distal end portion;

a balloon member mounted at said distal end portion of the tubular catheter body, said balloon member having an annular restriction which has a diameter smaller than that of a remainder of the balloon member, said annular restriction being at a middle region of the balloon member and in a plane approximately perpendicular to the longitudinal axis of the elongated tubular catheter body, said balloon member being sized and shaped for endoscopic guidance to the ventricle of the brain and said annular restriction being sized and shaped to enter, engage and dilate the hole in the ventricle of the brain;

said balloon member having a proximal portion and a distal end, said balloon member being secured to the tubular catheter body along said proximal portion of the balloon member, said distal end of the balloon member being unsecured to said tubular catheter body to provide a balloon unsecured distal tip, and wherein said balloon member is stretched longitudinally between its balloon unsecured distal tip which engages the distal end portion tip of the tubular catheter body and its proximal portion secured to the tubular catheter body; and said balloon unsecured tip encloses said distal end portion tip of the tubular catheter body, said balloon unsecured distal tip engages said distal end portion tip of the tubular catheter body prior to inflation of said balloon member, and said balloon unsecured distal tip is spaced apart from said distal end portion tip of the tubular catheter body upon inflation of said balloon member.

2. The catheter in accordance with claim 1, wherein said distal end portion tip of the tubular catheter body is closed, and said distal end portion of said tubular catheter body has at least one hole therethrough for passing inflation fluid into said balloon member, said at least one hole being at a location distal of the location at which the balloon proximal portion is secured to the tubular catheter body.

3. The catheter in accordance with claim 2, wherein said tubular catheter body has another hole, said at least one hole being positioned generally distal of said annular restriction and said another hole generally proximal of said annular restriction.

4. The catheter in accordance with claim 1, further including an adhesive securing said balloon member to the tubular catheter body along said proximal portion of the balloon member.

5. The catheter in accordance with claim 1, wherein said annular restriction has a diameter approximately one-half of the remainder of the balloon member when inflated.

6. A process for manufacturing a dilatation balloon catheter adapted to dilate a hole having:

an elongated tubular catheter body with a proximal end portion, a distal end portion and a tip of said distal end portion;

a balloon member mounted at said distal end portion of the tubular catheter body, said balloon member having an annular restriction which has a diameter smaller than that of a remainder of the balloon member, said annular restriction being at a longitudinally middle region of the balloon member and along a plane approximately perpendicular to a longitudinal axis of the elongated tubular catheter body, said annular restriction is adapted to engage a hole;

said balloon member having a proximal portion and a distal end, said balloon member being secured to the tubular catheter body along said proximal portion of the balloon member, said distal end of the balloon member being unsecured to said tubular catheter body to provide a balloon unsecured distal tip; and said balloon unsecured tip encloses said distal end portion tip of the tubular catheter body, said balloon unsecured distal tip engages said distal end portion tip of the tubular catheter body prior to inflation of said balloon member, and said balloon unsecured distal tip is spaced apart from said distal end portion tip of the tubular catheter body upon inflation of said balloon member;

wherein the process comprises:

providing a spindle which is generally dumbbell-shaped with at least two annular lengths at least partially defined at an end of each by a diametrically recessed annular region which has a diameter less than those of said annular lengths;

passing the spindle into and out of a supply of solution including material of the balloon member until a layer of said balloon material is formed on the spindle;

removing said layer of balloon material from said spindle to provide said balloon member; and securing said balloon member to the tubular catheter body along said proximal portion of the balloon member, wherein said securing includes engaging said distal end of the balloon member with the distal tip of the tubular catheter body, stretching the balloon member longitudinally, and affixing the proximal portion of the balloon member to the tubular catheter body while the balloon member is so stretched.

7. The process according to claim 6, wherein the supply of solution of the passing step includes silicone compound as said material of the balloon member.

8. The process according to claim 6, further including inflating the balloon wherein the distal end portion of the tubular catheter body is enclosed within the balloon member after said balloon inflating.

9. The process according to claim 8, wherein said inflating is carried out inside a tube.

10. A method of dilating a hole in a ventricle of the brain, comprising:

providing a dilation balloon catheter comprising an elongated tubular catheter body having a longitudinal axis, a proximal end portion, a distal end portion and a tip of said distal end portion; and a balloon member mounted at said distal end portion of the tubular catheter body, said balloon member having an annular restriction which has a diameter smaller than that of a remainder of the balloon member and positioned at a longitudinally middle region of the balloon member and in a plane approximately perpendicular to the longitudinal axis of the elongated tubular catheter body, said balloon member having a proximal portion and a distal end, said balloon member being secured to the tubular catheter body along said proximal portion of the balloon member, and said distal end of the balloon member being unsecured to said tubular catheter body to provide a balloon unsecured distal tip;

guiding said tubular catheter body and balloon member toward the ventricle of the brain with said balloon member stretched longitudinally between its balloon unsecured distal tip which engages the distal end portion tip of the tubular catheter body and its proximal portion secured to the tubular catheter body, such that said balloon unsecured tip encloses said distal end portion tip of the tubular catheter body and engages said distal end portion tip of the tubular catheter body prior to inflation of said balloon member;

positioning said balloon member and its annular restriction in the hole in the ventricle of the brain; and inflating said balloon member to dilate said hole and to space said balloon unsecured distal tip apart from said distal end portion tip of the tubular catheter body upon inflation of said balloon member.

11. The method according to claim 10, wherein the tubular catheter body and balloon member are endoscopically guided toward the ventricle of the brain.

12. The method according to claim 10, wherein said tubular catheter body is flexible.

13. The method according to claim 10, wherein said distal end portion tip of the tubular catheter body is closed, and said distal end portion of said tubular catheter body has at least one hole therethrough for passing inflation fluid into said balloon member, said at least one hole being at a location distal of the location at which the balloon proximal portion is secured to the tubular catheter body.

14. The method according to claim 13, wherein said tubular catheter body has another hole, said at least one hole being positioned generally distal of said annular restriction and said another hole generally proximal of said annular restriction.

15. The method according to claim 10, wherein said balloon member is secured to the tubular catheter body along said proximal portion of the balloon member by an adhesive.

16. The method according to claim 10, wherein said annular restriction has a diameter approximately one-half of the remainder of the balloon member when inflated.

* * * * *